United States Patent
Byers et al.

[11] Patent Number: 5,443,493
[45] Date of Patent: Aug. 22, 1995

[54] COCHLEA STIMULATING ELECTRODE ASSEMBLY, INSERTION TOOL, HOLDER AND METHOD OF IMPLANTATION

[75] Inventors: Charles L. Byers; James W. Beazell, Los Angeles; Matthew C. Fleming, Antioch, all of Calif.

[73] Assignee: Alfred E. Mann Foundation For Scientific Research, Sylmar, Calif.

[21] Appl. No.: 999,461

[22] Filed: Dec. 29, 1992

Related U.S. Application Data

[63] Continuation of Ser. No. 915,026, Jul. 15, 1992, which is a continuation of Ser. No. 780,825, Oct. 23, 1991, abandoned, which is a continuation of Ser. No. 411,875, Sep. 22, 1989, abandoned.

[51] Int. Cl.$^6$ ............................................. A61N 1/05
[52] U.S. Cl. ..................................... 607/137; 128/898
[58] Field of Search ............................. 607/56–57, 607/137; 128/898

[56] References Cited

U.S. PATENT DOCUMENTS

| | | | |
|---|---|---|---|
| 3,346,704 | 10/1967 | Mahoney | 600/25 |
| 3,483,494 | 12/1969 | Cromie | 128/852 |
| 3,752,939 | 8/1973 | Bartz | 600/25 |
| 3,827,428 | 8/1974 | HEn et al. | 128/642 |
| 4,010,757 | 3/1977 | Jula et al. | 128/785 |
| 4,644,957 | 2/1983 | Ricciardelli et al. | 128/784 |
| 4,686,765 | 8/1987 | Byers | 128/420.006 |
| 4,898,183 | 2/1990 | Kuzma | 128/420.006 |
| 4,923,469 | 5/1992 | Frachet et al. | 128/420.006 |

Primary Examiner—William E. Kamm
Attorney, Agent, or Firm—Robert R. Meads

[57] ABSTRACT

A cochlear electrode comprising a spirally curved distal tip portion carrying electrical conductors for stimulating the cochlea, a lead offset from the distal tip portion and a bridge therebetween and extending from the distal tip adjacent the proximal terminus thereof. The bridge defines a slide for guiding the distal tip portion into and out of an insertion tool during implantation of the electrode while the proximal terminus defines a push point for a push rod included in the insertion tool for sliding the distal tip out of the tool and into the cochlea.

14 Claims, 3 Drawing Sheets

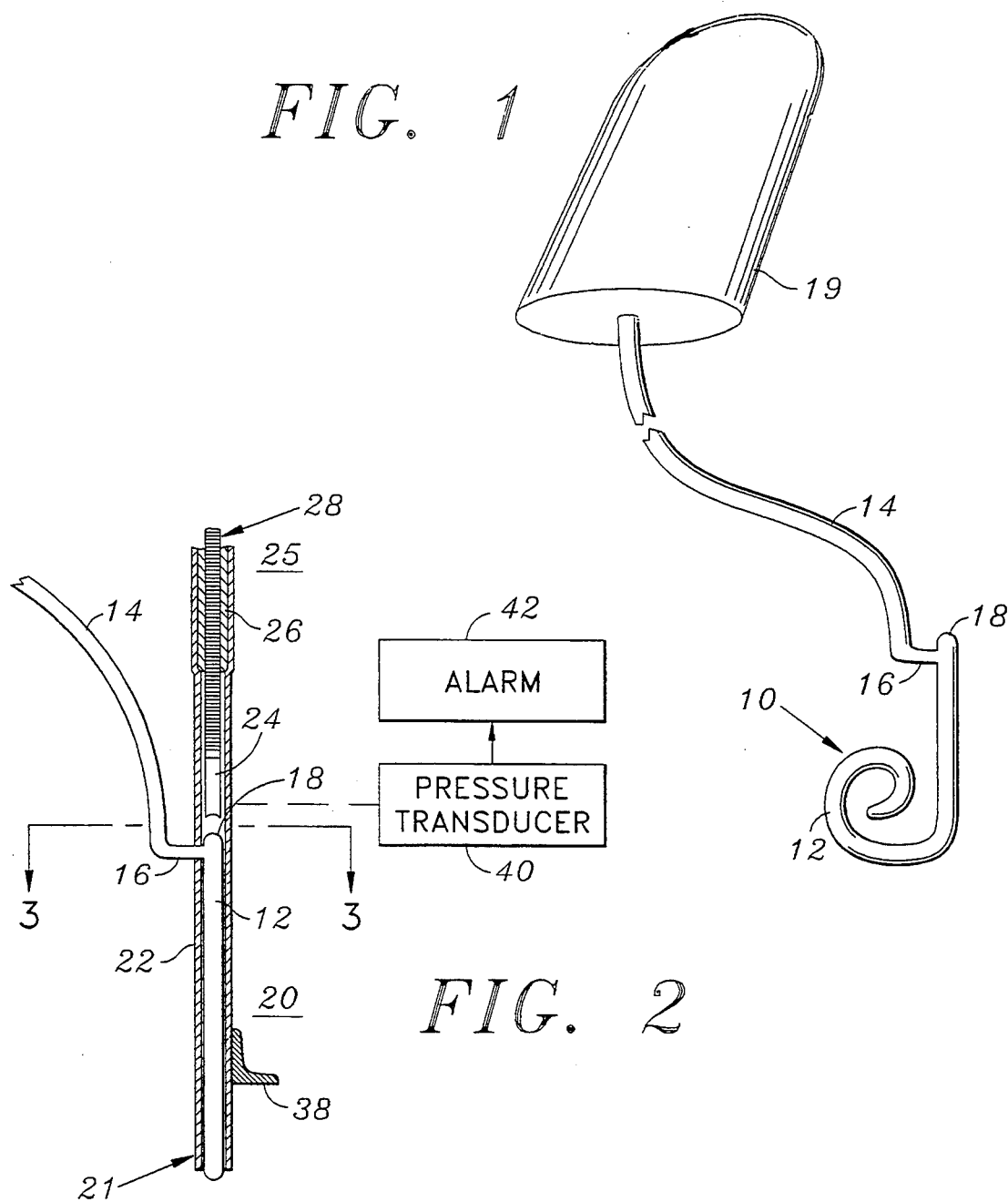
FIG. 1
FIG. 2
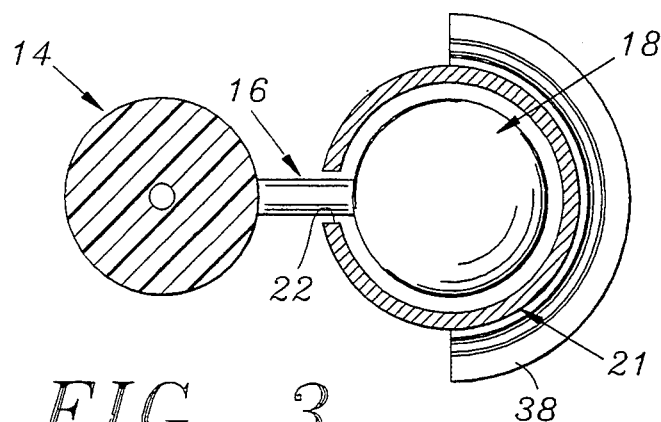
FIG. 3

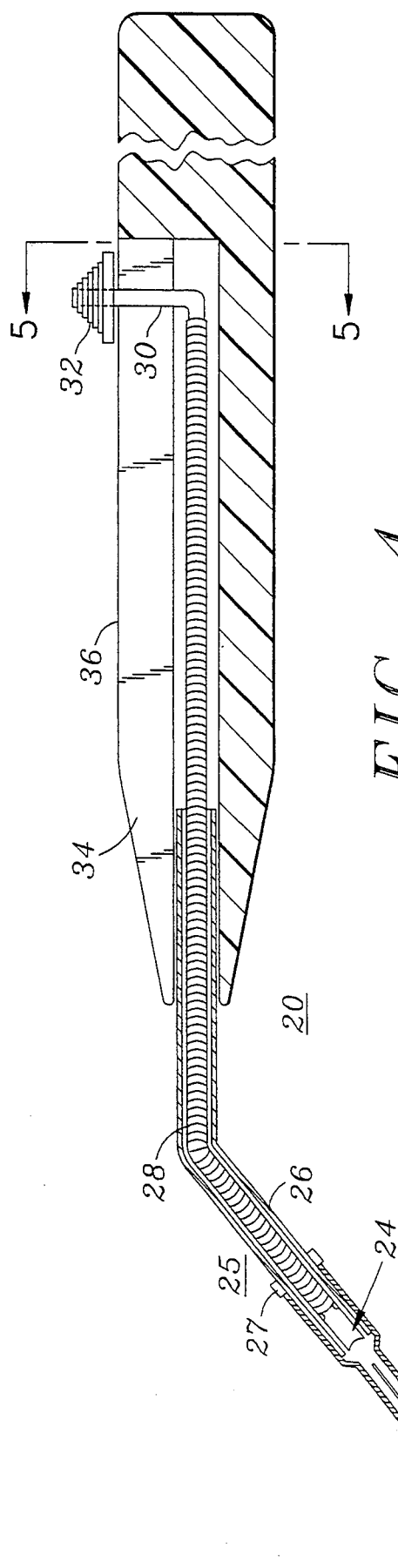
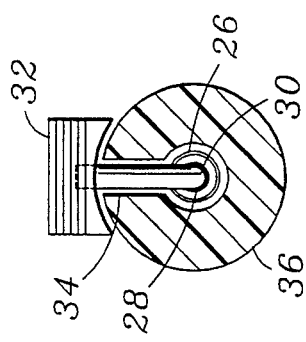

COCHLEA STIMULATING ELECTRODE ASSEMBLY, INSERTION TOOL, HOLDER AND METHOD OF IMPLANTATION

This is a continuation of application Ser. No. 07/915,026 filed on Jul. 15, 1992 which is a continuation of Ser. No. 07/780,825, filed Oct. 23, 1991 now abandoned, which is a continuation of Ser. No. 07/411,875, filed Sep. 22, 1989, now abandoned.

BACKGROUND

The present invention relates to implantable cochlea stimulating electrodes for improving the hearing of the hearing impaired and, more particularly, to an improved cochlea stimulating electrode assembly, insertion tool, holder and method of implantation.

U.S. Pat. No. 4,400,590 issued Aug. 23, 1983 for "Apparatus For Multichannel Cochlear Implant Hearing Aid System" describes and illustrates a multichannel intra-cochlear electrode for electrically stimulating predetermined locations of the auditory nerve within the cochlea of the ear. The electrode comprises a plurality of exposed electrode pairs spaced along and imbedded in a resilient curved base for implantation in accordance with the method of surgical implantation described in U.S. Pat. No. 3,751,605 issued Aug. 7, 1973 for "Method Of Inducing Hearing". By that method, bone above the round window of the cochlea is surgically exposed and removed to permit free access to the round window. The tip of the curved base of the electrode is inserted through the round window and into the cochlea. By simultaneously gently gripping sides of the base and pushing axially thereon the balance of the electrode base is eased through the round window into the lower scala of the cochlea to follow along the basilar membrane. The electrode pairs are very fragile and are often subject to damage during such implantation. Also, the implantation procedure is known to be very difficult to perform, requiring utmost skill on the part of the surgeon. In fact few surgeons have been able to master the implantation technique.

The present invention provides an improved cochlea stimulating electrode assembly and insertion tool which eliminates the simultaneous gripping and pushing of the electrode during implantation, greatly reduces the difficulty of the procedure and thereby provides an improved method of electrode implantation which is free of electrode damage. The electrode assembly design also permits the surgeon to easily attach the lead of the assembly to a patient's skull at the cochlea entrance during implant of the assembly.

SUMMARY OF INVENTION

The present invention comprises an improved cochlea stimulating electrode assembly and electrode insertion tool. The electrode assembly comprises a resilient elongated spirally curved distal tip portion and a lead offset from and connected to a side of the tip by a relatively narrow bridge. The lead connects to an electronic stimulator package and carries a plurality of conductors from the stimulator through the bridge to the tip portion where the conductors terminate in cochlea stimulating electrodes spaced along the tip portion. Preferably, the bridge is substantially narrower than the tip portion of the electrode assembly and connects to the side thereof adjacent to a proximal terminus of the tip.

In function, the bridge combines with the insertion tool to provide means for guiding and gently sliding the tip portion of the electrode assembly into a cochlea during surgical implantation of the electrode assembly. In this regard, the insertion tool includes a longitudinally extending insertion tube having an axially extending slot in one side thereof and a push rod for sliding into the insertion tube to engage the proximal terminus of the tip portion and by pushing thereon gently sliding the tip portion from the insertion tube and into the cochlea during electrode implantation according to the method of the present invention.

In addition, the bridge defines a step in the electrode assembly which aids in the surgical positioning and securing of the assembly at the entrance to the cochlea.

More particularly, with the improved cochlea stimulating electrode and insertion tool, the method of implantation of the electrode assembly comprises surgically exposing and removing bone to expose the round window of a cochlea and inserting a distal end of the axially slotted longitudinally extending insertion tube into the round window. The resilient spirally curved distal tip portion of electrode extends axially in the distal end of the insertion tube and the bridge rides smoothly in the axial slot in the insertion tube. A light axial pushing with the push rod on the proximal terminus of the tip portion slides first the distal tip portion followed by the entire length of the electrode tip out of the insertion tube and into the scala of the cochlea. Thus, by use of the insertion tool and improved electrode assembly with its offset lead, distal tip and bridge portions, the distal tip portion carrying the fragile electrical conductor tips is simply and safely guided into the cochlea by a light pushing on a proximal terminus of the distal tip portion which is free of fragile conductors. Once within the cochlea, the electrode is surgically secured as by packing tissue around the bridge portion of the electrode at the round window to there secure the electrode in place.

Preferably during implantation of the electrode assembly, it is desired that the stimulator package be secured and held separate from the electrode assembly. In a preferred method according to the present invention, the stimulator package is secured in place by a magnet such as a ring of a magnetic material worn by the surgeon. The ring has a flat side against which the stimulator package is placed. The electronics within the stimulator package include a magnet which attracts and holds the package against the ring during implantation of the electrode. When the electrode has been implanted, the package is separated from the ring and placed in a surgically prepared pocket and covered with tissue to complete the implant operation.

Another method of holding the stimulator package is to have a tool that clips onto tissue and is attractive to a magnet. The surgeon can then clip the tool onto tissue near the cochlear entrance and have the tool hold the package for the surgeon.

BRIEF DESCRIPTION OF DRAWINGS

FIG. 1 is a plan view showing the improved structure of the cochlear electrode assembly of the present invention having a spirally curved distal tip portion, a lead offset from the tip by a narrow bridge and connected to a stimulator package.

FIG. 2 is a plan view of the electrode of FIG. 1 with the spirally curved end straightened and in an axially slotted insertion tube of an insertion tool for the electrode, the tube being shown in longitudinal cross-section.

FIG. 3 is an enlarged cross-sectional view of the electrode and tube along the line 3—3 in FIG. 2.

FIG. 4 is a sectional side view of the insertion tool of the present invention.

FIG. 5 is a cross-sectional view taken along the line 5—5 in FIG. 4.

DETAILED DESCRIPTION OF INVENTION

Figure 6:
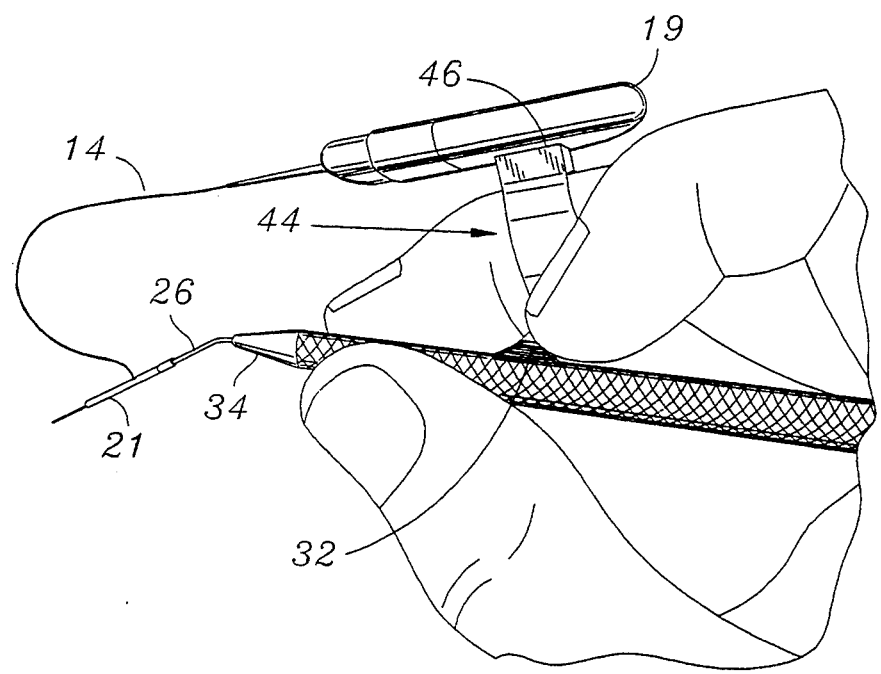
FIG. 6 is a side view of the insertion tool held between the thumb and third finger of a surgeon using his forefinger to actuate the insertion tool and slid the electrode assembly therefrom and his third finger to carry a ring holding in place the stimulator package.

As illustrated in FIG. 1, the improved cochlea stimulating electrode assembly of the present invention is represented by the numeral 10. It comprises a resilient, elongated, spirally curved distal tip portion 12 of circular cross-section, a lead 14 offset laterally from the tip portion and a relatively narrow bridge 16 between the lead and a side of the tip. The lead 14 is connected at its proximal end to a hermetically sealed package 19 for the electronics comprising a cochlear stimulator and carries a plurality of electrical conductors (not shown) from the stimulator through the bridge 16 to the tip portion where the conductors terminate in electrode pairs for stimulating the cochlea at spaced locations along the tip portion.

As illustrated in FIGS. 1 and 2, the bridge 16 connects to a distal end of the lead 14 and to the tip portion 12 adjacent a rounded proximal terminus 18 of the tip portion. Preferably, the bridge 16 is of rectangular cross-section having a width substantially less than the outside diameter of the tip portion 12 and defines a slide extending from the tip portion for smoothly guiding the tip portion from an insertion tool 20 during insertion of the tip into and through a round window of a cochlea during implantation of the electrode in the lower scala of the cochlea. For example, the outside diameter of the tip portion may be about 0.8 mm and the width of the bridge 16 may be about 0.5 mm. As will be described hereinafter, such a dimensional relationship is important to the efficient operation of the insertion tool in introducing the tip portion 14 of the electrode assembly into the cochlea.

Figure 7:
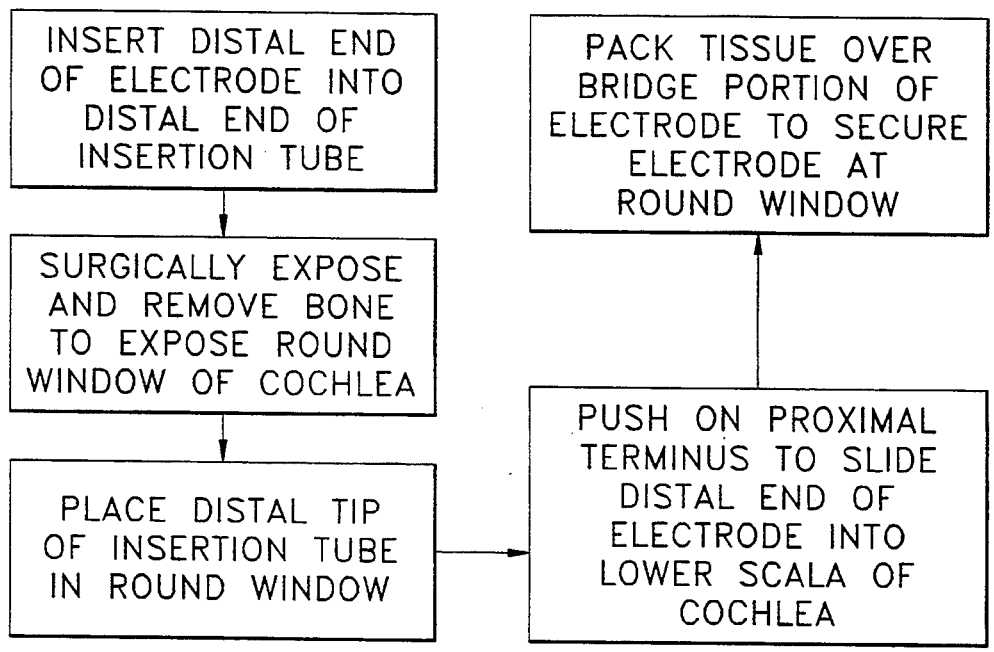
FIG. 7 is a flow diagram of the method of implantation for the electrode of FIG. 1 using the insertion tool of FIG. 4.

More particularly, as illustrated in FIGS. 2 and 3, the insertion tool 20 includes an insertion tube 21 of circular cross-section slightly larger than the circular cross section of the distal tip portion 12 and having a axially extending elongated slot 22 for receiving and guiding the slide defined by the bridge 16 up and down the tube 21. In this regard, as depicted in FIG. 7, a first or preliminary step in the method of implantation of the present invention comprises the step of preloading the distal tip portion 12 into the distal end of the insertion tube 21. This is accomplished by introducing the proximal terminus 18 into the open end of the tube 21 and then uncoiling the distal tip portion of the resilient electrode assembly to straighten the distal tip so that it can be easily slipped into the tube 21 with the bridge portion 16 riding in the slot 22 as a slide to guide the distal tip into the tube. More particularly, since the distal tip portion 12 is normally coiled into a spiral, within the tube 21 the tip portion exerts transverse forces on the interior of the tube. If possible, parts of the tip portion would wedge into the axial slot 22 interfering with the smooth sliding motion of the tip in the tube. For this reason, the lateral dimensions of the axial slot 22 and bridge 16 are much smaller than the outer diameter of the tip portion 12. As previously indicated, the width of the bridge may be about 0.5 mm. The bridge 16 like the tip portion 12 may be formed of a silastic material while the tube 21 may be formed of a polymer such as Teflon. Both are self-lubricating and the bridge and sides of the axial slot in the tube formed thereof will slide against each other with minimum friction. Therefor, the lateral dimension of the axial slot 22 also may be about 0.5 mm. This insures that the tip portion 12 can not wedge into the axial slot 22 as the tip portion is gently moved into and out of the tube 21.

Within the tube 21, the proximal terminus 18 lies adjacent a cup-shaped end 24 of a push rod assembly 25. As illustrated most clearly in FIGS. 2 and 4, in addition to the end 24, the push rod assembly 25 includes a bent connector tube 26, a flexible longitudinally extending coiled wire 28, a bent connecting rod 30 and a push button 32. The end 24 rides in the distal open end of the connector tube 26 and is secured to the wire 28 which is coiled and extends longitudinally within the tube 26 past a 30° bend therein to connect to the connecting rod 30. One end of the connecting rod 30 is received within and secured to the coils of the wire 28. From the wire 28, the rod 30 bends at a 90° angle to terminate at the push button 32. The push button 32 is moveable forward and backward in a longitudinally extending slot 34 in the front end of a pencil-shaped handle 36 also included in the insertion tool 20. In this regard, a surgeon implanting the electrode assembly 10 after preloading the distal tip portion 12 into the distal end of the insertion tube 21, pushes the open proximal end of the tube 21 onto the open distal end of the connector tube 26 until the proximal end of the tube 21 engages a stop ring 27 on the connector tube 26. The connector tube 26 is secured in the open distal end of the pencil-shaped handle 36 with the end 24 of the push rod assembly 25 at the distal end of the connector tube. Then, according to the method of FIG. 7, after surgically exposing and removing bone to expose the round window of the cochlea, the surgeon takes the insertion tool 20, holding the handle 36 much like a pencil between his thumb and third finger, and places the open distal end of the insertion tube 21 into the round window. He then moves the tube 21 within the round window until a stop flange 38 extending laterally from the tube 21 adjacent a distal end thereof rests against the bony surface of the medial wall of the middle ear to prevent accidental damage to cochlear structure by insertion of the tube into the cochlea. Next, with his forefinger, the surgeon pushes forward on the push button 32. The forward movement of the push button 32 is translated into forward sliding movement of the connecting rod 30 along the slot 34 to move the coil wire 28 forward causing the cup-shaped end 24 to move forward and receive the proximal terminus 18 of the distal tip portion 12 of the electrode 10. Continued forward movement of the push button 32 simply slides the distal tip portion 12 along the insertion tube 21 with the slide defined by the bridge 16 guiding the distal tip portion out of the insertion tube through the round window and into the lower scala of the cochlea. There, the electrode is secured by the surgeon packing tissue around a step defined by the bridge portion 16 and surgically closing the wound to hold the electrode at the round window with the distal tip portion extending into the lower scala.

During the above described electrode insertion process, no lateral gripping forces are exerted upon the distal tip portion 12 of the electrode which might damage the fragile electrical conductors or electrode pairs carried by the distal tip. The force sliding the electrode into the cochlea is exerted upon the proximal end of the distal tip where there are no electrical conductors or electrode pairs. The pushing force is axial along the straightened distal tip which is guided by the bridge portion 16 with minimal sliding friction along the insertion tube and into the cochlea. In this manner, the present invention provides an improved cochlea stimulating electrode structure and insertion assembly which results in an implantation of the electrode within the cochlea without electrode damage.

As shown diagrammatically in FIG. 2, to further insure that such damage does not occur or that any cochlea structure is accidentally damaged during the implantation as just described, the insertion tool may further include a miniature pressure transducer 40 at the end 24 of the push rod assembly 25 or other suitable location. For example, the transducer 40 may comprise a pair of normally open electrical contacts in series with a battery and light or other alarm 42. The contacts may be urged apart by a spring and one of the contacts may be moveable with the push rod against the force of this spring. The contact will close against each other to actuate the alarm only when the pressure exerted in the proximal terminus by the push rod exceeds a predetermined value. Alternatively, the transducer may be of a form that will generate an electrical signal which is a function of the pressure exerted on the proximal terminus 18 by the push rod assembly 25. When a predetermined threshold indicating a maximum pressure limit is reached, the magnitude of the electrical signal is sufficient to actuate the alarm 42 which will alert the surgeon to reduce his finger force on the push rod assembly. Still another form of transducer configuration may include an electrically actuated brake for halting movement of the push rod when a predetermined pressure limit is exceeded and detected by the transducer.

Preferably during implantation of the electrode assembly 10, it is desired that the stimulator package 19 be secured separate from the electrode assembly. As illustrated in FIG. 6, in a preferred method of the present invention, the package 19 is secured in place by a ring 44 worn on the third finger of the surgeon. The ring is formed of a magnetic material such as 400 series stainless steel and has a flat side 46 against which the package is placed. The electronics within the package 19 includes a magnet which attracts the ring and holds the package firmly in place against the flat side 46 of the ring 44 during implantation of the electrode assembly 10. When the implantation of the electrode assembly is complete, the package 19 is removed from the ring 44 and placed in a surgically prepared pocket adjacent the electrode and covered with tissue to complete the implant procedure.

Alternatively, the holder for the stimulator package may comprise a tissue or towel clip having a pari of tongs pivotally connected at a mid-point. The pivot or a portion of one of the handles of the tongs may comprise a magnetic material or may carry a magnet. Like the ring 44, such magnetic material or magnet will hold the stimulator package adjacent to the cochlea when the clip is secured to tissue near the entrance to the cochlea. Again when the implantation of the electrode assembly is complete, the package is removed from the magnet and placed in a surgically prepared pocket adjacent the electrode and covered with tissue.

While a particular electrode assembly, insertion tool, holder and method have been described in detail, the present invention is not be limited to the specifics set forth hereinabove. For example, rather than being moveable by the push button 32, the connecting rod 30 may be moved by a finger actuated trigger mechanism. And of course, the push button may be situated so as to be moved by a finger other than the surgeon's forefinger. Accordingly, the present invention is to be limited in scope only by the following claims.

We claim:

1. A cochlea stimulation electrode having a resilient curved distal tip portion for insertion into and stimulation of a cochlea, the stimulating electrode further comprising:

a lead offset laterally from the distal tip portion for connection to a stimulator for the electrode; and a bridge extending from the lead and connecting to the distal tip portion adjacent a proximal terminus thereof, the bridge defining a slide for guiding the distal tip portion from an insertion tool during insertion of the distal tip portion into a round window of the cochlea and the proximal terminus defining a push point for a push rod assembly for forcing the distal tip portion from the insertion tool.

2. The electrode of claim 1 wherein the distal tip portion has a generally circular cross-section and the bridge has a width less that an outer diameter of the tip portion.

3. The electrode of claim 2 wherein the proximal terminus has a rounded tip.

4. An insertion tool for inserting a cochlea stimulating electrode through a round window and into a cochlea, comprising:

a longitudinally extending insertion tube for axially receiving and guiding a distal tip portion of a resilient cochlea stimulating electrode from a distal end of the tube into a cochlea, the insertion tube including an axial slot for receiving and axially guiding a slide means extending from the distal tip portion of the cochlea stimulating electrode; and a push rod assembly including a distal end for insertion into a proximal end of the insertion tube to push upon a proximal terminus of the distal tip portion of the electrode to force the distal tip portion from the distal end of the insertion tube and into the cochlea through the round window.

5. The insertion tool of claim 4 further including a stop flange from a distal end portion of the insertion tube for engaging a bony surface and halting inward movement of the insertion tube as the insertion tube is inserted into the round window.

6. The insertion tool of claim 4 further including alarm means and pressure transducer means connected to the push rod for actuating the alarm means when pressure of the push rod on the proximal terminus reaches a predetermined value.

7. The insertion tool of claim 4 wherein the distal end of the push rod is cup-shaped to receive a rounded proximal terminus of the distal tip portion of the electrode.

8. The insertion tool of claim 4 further including an elongated handle having an open distal end for receiving a proximal end of the push rod assembly and hand-moveable means carried by the handle and connected to the push rod assembly for axially moving the distal end of the push rod assembly in the insertion tube.

9. The insertion tool of claim 8 further including a bent connector tube extending from the open distal end of the handle and wherein the push rod assembly further includes a distal end member, a flexible axially extending central portion connected to the distal end member for riding in the bent connector tube and a proximal end connected to the hand-moveable means.

10. The insertion tool of claim 9 wherein the handle is pencil-shaped for gripping between the thumb and third finger of an operator with the forefinger free to push upon and move a push button comprising the hand-moveable means along a slot in the handle.

11. A method of implanting a cochlea stimulating electrode in the cochlea using an insertion tool including a longitudinally extending insertion tube having a slot in a side thereof extending axially from a distal end thereof and a push rod assembly for insertion into a proximal end of the insertion tube, the electrode including a resilient curved distal tip portion for insertion into and stimulation of the cochlea, a lead offset laterally from the distal tip portion for connection to a stimulator for the electrode, and a bridge extending from the lead and connecting to the distal tip portion adjacent a proximal terminus thereof, the bridge defining a slide for guiding the distal tip portion from an insertion tool during insertion of the distal tip portion into a round window of the cochlea and the proximal terminus defining a push point for the push rod assembly for forcing the distal tip portion from the insertion tool, the method comprising the steps of:

surgically exposing and removing bone over the cochlea to expose the round window of the cochlea;

inserting the distal end of the longitudinally extending insertion tube into the round window with (1) the resilient curved distal tip portion of the electrode axially extending in the distal end of the insertion tube, (2) the bridge riding in the axial slot of the insertion tube and (3) the lead extending from the bridge and offset laterally from the tip portion connecting to a stimulator for the electrode;

pushing with the push rod assembly on the proximal terminus of the distal tip portion of the electrode to slide the electrode from the insertion tube into the cochlea with the bridge adjacent the round window; and packing tissue over the bridge to secure the electrode at the round window.

12. The method of claim 11 further including preloading the curved distal tip portion of the electrode in the insertion tube by (1) inserting the proximal terminus into the distal end of the insertion tube with the bridge in a distal open end of the axial slot in the insertion tube and (2) axially feeding the distal tip portion into the insertion tube with the bridge riding in the slot until the entire distal tip portion is within the insertion tube.

13. The method of claim 12 wherein pushing on a proximal terminus comprises pushing forward on a push button in a handle connected to the insertion tube to move forward a push rod bearing on the proximal terminus of the distal tip portion of the electrode.

14. A method of implanting a cochlear stimulating system including a package housing electronics for generating stimulating signals and an electrode for transmitting the stimulating signals to the cochlea, the electrode comprising a resilient curved distal tip portion for insertion into and stimulation of the cochlea, a lead offset laterally from the distal tip portion for connection to a stimulator for the electrode, and a bridge extending from the lead and connecting to the distal tip portion adjacent a proximal terminus thereof, the bridge defining a slide for guiding the distal tip portion from the insertion tool during insertion of the distal tip portion into a round window of the cochlea and the proximal terminus defining a push point for a push rod assembly for forcing the distal tip portion from the insertion tool, the method comprising the steps of:

holding the package adjacent the cochlea while the electrode is implanted;

surgically exposing and removing bone over the cochlea to expose the round window of the cochlea;

inserting the distal end of the insertion tube into the round window with (1) the resilient curved distal tip portion of the electrode axially extending in the distal end of the insertion tube, (2) the bridge riding in the axial slot of the insertion tube and (3) the lead extending from the bridge and offset laterally from the tip portion connecting to a stimulator for the electrode;

pushing with the push rod assembly on the proximal terminus of the distal tip portion of the electrode to slide the electrode from the insertion tube into the cochlea with the bridge adjacent the round window;

packing tissue over the bridge to secure the electrode at the round window; and implanting the package adjacent the electrode.

* * * * *